US00PP19109P2

(12) United States Plant Patent
Kramer

(10) Patent No.: US PP19,109 P2
(45) Date of Patent: Aug. 19, 2008

(54) ***GERANIUM* PLANT NAMED 'ROSETTA'**

(50) Latin Name: *Geranium wallichianum*
Varietal Denomination: Rosetta

(75) Inventor: Hans Kramer, Ede (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 11/705,905

(22) Filed: Feb. 14, 2007

(51) Int. Cl.
*A01H 5/00* (2006.01)

(52) U.S. Cl. ..... Plt./324
(58) Field of Classification Search ..... Plt./324
See application file for complete search history.

*Primary Examiner*—Kent L Bell
(74) *Attorney, Agent, or Firm*—C. A. Whealy

(57) ABSTRACT

A new and distinct cultivar of *Geranium* plant named 'Rosetta', characterized by its upright and broadly outwardly spreading plant habit; freely basal branching growth habit; freely flowering habit; pink-colored flowers with light pink-colored centers; and good garden performance.

1 Drawing Sheet

Botanical designation: *Geranium wallichianum.*
Cultivar denomination: 'Rosetta'.

BACKGROUND OF THE INVENTION

The present invention relates to a new and distinct cultivar of *Geranium,* botanically known as *Geranium wallichianum,* and hereinafter referred to by the name 'Rosetta'.

The new *Geranium* originated from a cross-pollination of the *Geranium wallichianum* cultivar Syabru, not patented, as the female, or seed, parent with an unnamed selection of *Geranium wallichianum,* not patented, as the male, or pollen, parent. The new *Geranium* was discovered and selected by the Inventor as a single flowering plant from within the progeny of the stated cross-pollination grown in a controlled environment in Ede, The Netherlands in July, 2001.

Asexual reproduction of the new *Geranium* by terminal cuttings in a controlled environment in Zandvoort, The Netherlands since January, 2004, has shown that the unique features of this new *Geranium* are stable and reproduced true to type in successive generations.

SUMMARY OF THE INVENTION

The cultivar Rosetta has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Rosetta'. These characteristics in combination distinguish 'Rosetta' as a new and distinct cultivar of *Geranium:*

1. Upright and broadly outwardly spreading plant habit.
2. Freely basal branching growth habit.
3. Freely flowering habit.
4. Pink-colored flowers with light pink-colored centers.
5. Good garden performance.

Plants of the new *Geranium* differ primarily from plants of the female parent, the cultivar Syabru in flower color as plants of the cultivar Syabru have dull pink-colored flowers with smaller light pink-colored eyes and more distinct venation.

Plants of the new *Geranium* differ primarily from plants of the male parent selection in flower color as plants of the male parent selection have bluish pink-colored flowers.

Plants of the new *Geranium* can be compared to plants of the *Geranium* cultivar Buxton Blue, not patented. In side-by-side comparisons conducted in The Netherlands, plants of the new *Geranium* differed primarily from plants of the cultivar Buxton Blue in flower color as plants of the cultivar Buxton Blue had blue and white-colored flowers.

BRIEF DESCRIPTION OF THE PHOTOGRAPHS

The accompanying colored photographs illustrate the overall appearance of the new *Geranium,* showing the colors as true as it is reasonably possible to obtain in colored reproductions of this type. Colors in the photographs may differ slightly from the color values cited in the detailed botanical description which accurately describe the colors of the new *Geranium.*

The photograph at the top sheet comprises a side perspective view of typical flowering plants of 'Rosetta' grown in an outdoor nursery.

The photograph at the bottom of the sheet is a close-up view of a typical flower of 'Rosetta'.

DETAILED BOTANICAL DESCRIPTION

The aforementioned photographs and following observations, measurements and values describe plants grown in Ede, The Netherlands in an outdoor nursery during the summer and early autumn. During the production of the plants, day temperatures ranged from 14° C. to 32° C. and night temperatures ranged from 4° C. to 15° C. Plants were about one year old when the photographs and the description were taken. In the detailed description, color references are made to The Royal Horticultural Society Colour Chart, 2001 Edition, except where general terms of ordinary dictionary significance are used.

Botanical classification: *Geranium wallichianum* cultivar Rosetta.

Parentage:

*Female, or seed, parent.*—*Geranium wallichianum* cultivar Syabru, not patented.

*Male, or pollen, parent.*—Unnamed selection of *Geranium wallichianum,* not patented.

Propagation:

*Type.*—By terminal cuttings.

*Time to initiate roots.*—About three weeks at temperatures of 20° C.

*Time to produce a rooted young plant.*—About six weeks at temperatures of 20° C.

*Root description.*—Fine, fibrous; white in color.

*Rooting habit.*—Freely branching, moderately dense.

Plant description:

*General appearance.*—Upright and broadly outwardly spreading plant habit.

*Growth and branching habit.*—Moderately vigorous growth habit. Freely basal branching habit with about ten lateral branches per plant.

*Plant height.*—About 18 cm.

*Plant width.*—About 43.5 cm.

*Lateral branches.*—Length: About 18.8 cm. Diameter: About 3 mm. Internode length: About 5.8 cm. Texture: Pubescent. Strength: Moderately strong. Color: 144A; upper surface and older stems overlain with 183A to 183B.

Foliage description:

*Arrangement.*—Opposite; simple.

*Length.*—About 5.5 cm.

*Width.*—About 6 cm.

*Shape.*—Orbicular to roughly reniform; palmately lobed.

*Apex.*—Acute.

*Base.*—Hastate.

*Margin.*—Palmately lobed; lobes bi-serrate.

*Venation pattern.*—Palmate.

*Texture, upper and lower surfaces.*—Densely pubescent.

*Color.*—Developing foliage, upper surface: 143A. Developing foliage, lower surface: 146B. Fully developed, upper surface: Between 137A and 143A; venation, between 137A and 143A. Fully developed, lower surface: 146A to 146B; venation, 146A to 146B.

*Petiole.*—Length: About 4.1 cm. Diameter: About 1.5 mm. Texture, upper and lower surfaces: Pubescent. Color, upper and lower surfaces: 144A to 144B; upper surface and older leaves, overlain with 178A.

Flower description:

*Flower arrangement.*—Single rotate flowers arranged in pairs arising from apical leaf axils. Flowers face upright or outward. Flowers not persistent. Flowers not fragrant.

*Quantity of flowers.*—Freely flowering habit; about twelve flower buds and open flowers per lateral branch.

*Flowering season.*—In The Netherlands, flowering is continuous from early May to late September.

*Flower longevity.*—Flowers last about one week on the plant.

*Flower diameter.*—About 3.3 cm.

*Flower depth* (*height*).—About 1.1 cm.

*Flower buds.*—Length: About 9 mm. Diameter: About 4 mm. Shape: Elliptic. Color: Between 143A and 144A.

*Petals.*—Quantity per flower: Five in a single whorl. Length: About 1.7 cm. Width: About 1.4 cm. Shape: Obcordate. Apex: Obtuse. Base: Attenuate. Margin: Entire. Texture, upper and lower surfaces: Mostly smooth; towards the base, densely pubescent. Color: When opening, upper surface: Between N74A and N78B; venation, N79B. When opening, lower surface: N78B; venation, N79C. Fully opened, upper surface: N78B; towards the base, close to N78D; venation, N79B. Color becoming closer to N81C with development. Fully opened, lower surface: N78C; venation, N79C.

*Sepals.*—Quantity per flower: Five, arranged in a single whorl. Length: About 1 cm. Width: About 4 mm. Shape: Ovate. Apex: Aristate. Base: Cuneate. Margin: Entire. Texture, upper surface: Mostly smooth; towards the margins, pubescent. Texture, lower surface: Pubescent. Color: When opening, upper surface: Between 143A and 144A. When opening, lower surface: 144A. Fully opened, upper and lower surfaces: 143B.

*Peduncles.*—Length: About 4.4 cm. Diameter: About 1.2 mm. Strength: Strong. Angle: About 10° from vertical. Texture: Pubescent. Color: 152A.

*Pedicels.*—Length: About 3 cm. Diameter: About 1 mm. Strength: Moderately strong. Angle: About 340° from vertical. Texture: Pubescent. Color: 144A.

*Reproductive organs.*—Androecium: Stamen quantity per flower: About ten. Filament length: About 6 mm. Filament color: N79C. Anther length: About 2 mm. Anther shape: Oblong. Anther color: Between N186A and 202A. Pollen amount: Scarce. Pollen color: 196D. Gynoecium: Pistil quantity per flower: One. Pistil length: About 6 mm. Stigma shape: Five-parted; reflexed. Stigma color: N79B to N79C. Style length: About 3 mm. Style color: 144A. Ovary color: Close to 143A to 143B.

*Fruits/seeds.*—Fruit and seed development have not been observed.

Disease/pest resistance: Plants of the new *Geranium* have not been observed to be resistant to pathogens and pests common to *Geraniums.*

Garden performance: Plants of the new *Geranium* have exhibited good tolerance to rain and wind and have been observed to tolerate temperatures ranging from about −15° C. to about 35° C.

It is claimed:

1. A new and distinct *Geranium* plant named 'Rosetta' as illustrated and described.

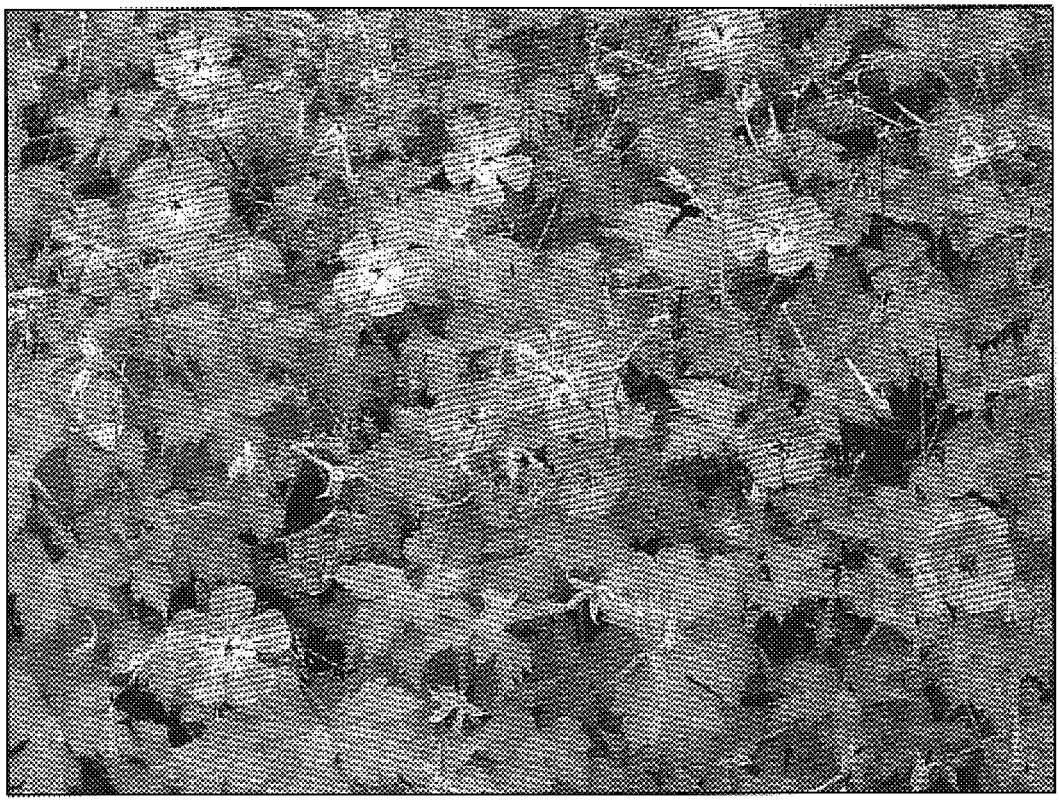
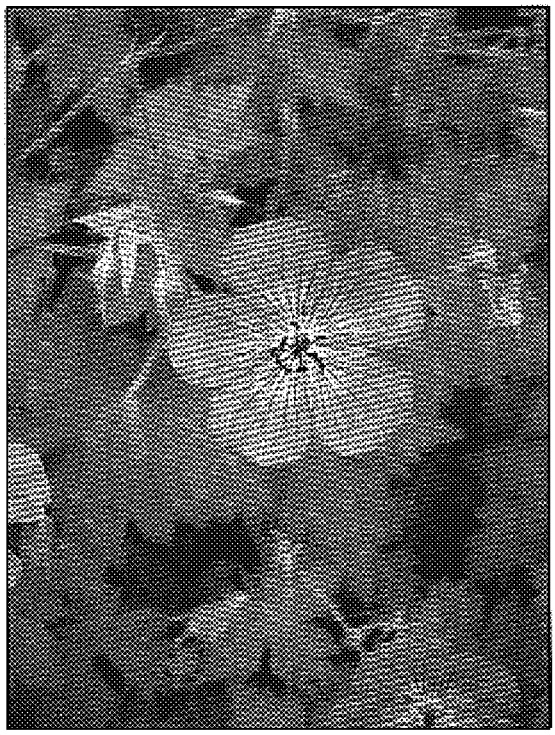

* * * * *